United States Patent [19]
Shin et al.

[11] Patent Number: 6,113,682
[45] Date of Patent: Sep. 5, 2000

[54] METHOD FOR PREPARATION OF COMPOSITE PIGMENTS FOR MAKE-UP COSMETICS AND MAKE-UP COSMETIC COMPOSITIONS CONTAINING COMPOSITE PIGMENTS MADE THEREBY

[75] Inventors: Dal Sik Shin, Seongnam; Dong Myong Kim, Suwon; Sung Ho Lee, Kunpo; Ok Sob Lee, Anyang; Kwang Soo Kim, Nonsan; Ju Hong Min, Taejeon, all of Rep. of Korea

[73] Assignees: Pacific Corporation, Seoul; Bokwang Chemical Co. Ltd., Choongchungbuk-do, both of Rep. of Korea

[21] Appl. No.: 09/187,482

[22] Filed: Nov. 6, 1998

[30] Foreign Application Priority Data

Jun. 9, 1998 [KR] Rep. of Korea ............. 98-21315

[51] Int. Cl.$^7$ ............... C09C 1/28; C09C 1/36
[52] U.S. Cl. ............. 106/446; 106/481; 106/482
[58] Field of Search ............. 106/446, 481, 106/482

[56] References Cited

U.S. PATENT DOCUMENTS

| | | | |
|---|---|---|---|
| 3,634,119 | 1/1972 | Klenke | 106/291 |
| 3,861,946 | 1/1975 | Waitkins et al. | 117/100 B |
| 4,882,133 | 11/1989 | Seagusa | 423/335 |
| 5,035,748 | 7/1991 | Burow et al. | 106/499 |
| 5,547,502 | 8/1996 | Chevallier et al. | 106/287.1 |
| 5,846,310 | 12/1998 | Noguchi et al. | 106/482 |
| 5,851,277 | 12/1998 | Muller-Rees et al. | 106/287.35 |

*Primary Examiner*—Mark L. Bell
*Assistant Examiner*—Michael J. DiVerdi
*Attorney, Agent, or Firm*—Foley & Lardner

[57] ABSTRACT

Disclosed herein is a method for preparation of composite pigments for make-up cosmetics having improved skin-adhesion and spreadability, and excellent skin color-expression, and improved water resistance by silicon polymer coated on the surface of the complex particle of flaky silica and titanium dioxide coated thereon.

12 Claims, 1 Drawing Sheet

METHOD FOR PREPARATION OF COMPOSITE PIGMENTS FOR MAKE-UP COSMETICS AND MAKE-UP COSMETIC COMPOSITIONS CONTAINING COMPOSITE PIGMENTS MADE THEREBY

BACKGROUND OF THE INVENTION

1. Field of the Invention

The present invention relates to a method for preparation of composite pigments for make-up cosmetics. More particularly, it relates to a method for preparation of composite pigments for make-up cosmetics having improved skin-adhesion and spreadability, and excellent skin color-expression, and improved water resistance by silicon polymer coated on the surface of the composite particle of flaky silica and titanium dioxide coated thereon. Also, it relates to a make-up cosmetic composition containing the above composite pigments.

2. Description of the Prior Art

In general, synthetic silica for make-up cosmetics has spherical, flaky or acicular particles and among them, porous or hollow silica having spherical particles with average particle diameter of 3~15 μm has been widely used. The spherical silica can increase fluidity of the content in make-up cosmetic composition due to its conformational property. But, the increased fluidity may maldistribute make-up film to a direction of force to be applied onto the skin, resulting in forming uneven film. And, spherical particles tend to roll on the skin, rather than to slide, resulting in poor spreadability. Further, minimum contact area of the spherical particles may cause poor skin-adhesion.

Accordingly, in order to overcome the foregoing defects of the spherical silica, a method for producing a flaky silica has been proposed in U.S. Pat. No. 4,882,133. The method comprises steps of coating silica hydrosol onto a surface of the roller and then heating to form silica hydrogel; vaporizating dispersion medium to shrink and scrap off the silica hydrogel, to give amorphous silica; and heating at a high temperature to give flaky silica with uniform thickness. The obtained flaky silica has improvement in spreadability and skin-adhesion, but has excessive light-transmittance, resulting in poor skin-color expression. So, this flaky silica is improper as an ingredient of make up cosmetics.

Meanwhile, in order to obtain extender pigments having improved skin-adhesion and spreadability, a coating technique has been developed rapidly. For example, there have been provided composite pigments prepared by coating talc, mica, sericite and the like with ultrafine titanium dioxide. The pigments such as talc, mica and sericite have good spreadability, while the ultrafine titanium dioxide has good skin-adhesion. Such composite pigments have been successful in obtaining good result in both skin-adhesion and spreadability, and so have been widely used in base make-up cosmetic products such as twin-cake, powder foundation, liquid foundation and makeup base. However, the pigment derived from clay mineral, for example, talc, mica or sericite has high gravity of 2.5~2.8, and the composite pigments prepared therefrom have also high gravity, to show heavy feeling onto the skin.

Under this circumstance, the present inventors have conducted extensive studies in order to solve the above problem or drawback and to provide new composite pigments having improved skin-adhesion and spreadability, and having appropriate transmittance to the skin color. As a result, they found that composite pigments prepared by coating flaky silica with ultrafine titanium dioxide can achieve the above objects, and in addition show light feeling onto the skin. Based on this finding, the present invention can be accomplished.

SUMMARY OF THE INVENTION

Thus, an object of the present invention is to provide a new composite pigment for make-up cosmetics having improved skin-adhesion and spreadability, and having appropriate transmittance to central wavelength region for the skin color to show good skin color-expression.

Further, another object of the present invention is to provide a method for preparing the above composite pigment.

And, still another object of the present invention is to provide make-up cosmetic compositions containing the above composite pigments.

The method for preparing composite pigments according to the present invention comprises steps of:

(1) reacting sodium silicate solution with aqueous sulfuric solution to form silica gel slurry;

(2) crushing said silica gel slurry to form coarse silica;

(3) grinding said coarse silica by means of impact mil and successively, air current-impact system of air jet mill to form flaky silica;

(4) coating said flaky silica with ultrafine titanium dioxide to form composite particles; and (5) coating said composite particles with silicon polymer to give composite pigments for make-up cosmetics.

These and other objects and features of the present invention will be apparent to the skilled in the art from the following detailed description.

DETAILED DESCRIPTION OF THE INVENTION

Figure 1:
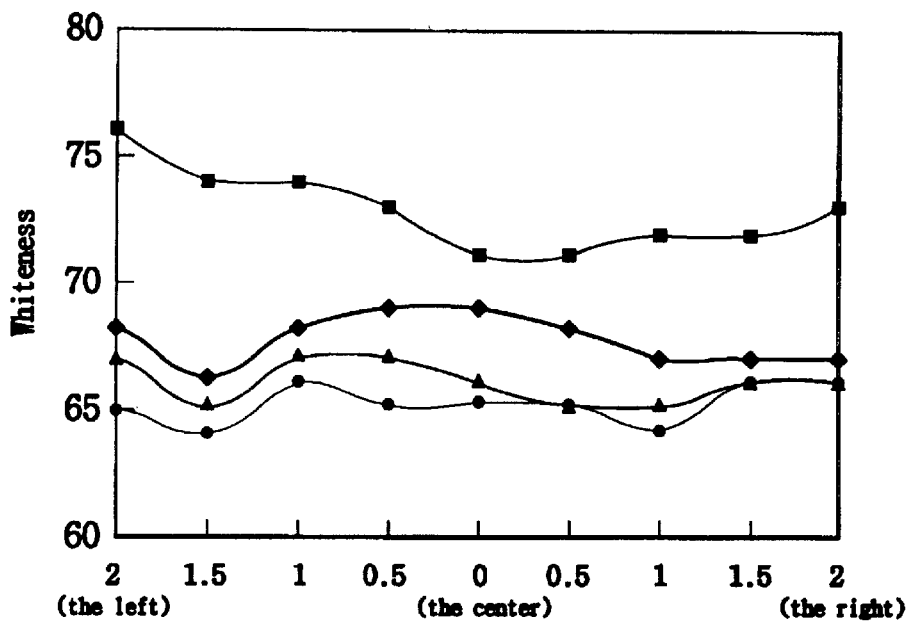
FIG. 1 is a graph showing the whiteness of various composite pigments at increasing distances from the center of a circle of an applied sample on skin.

The present invention will be described in more detail hereinafter.

The present invention is characterized in that the composite pigments have flaky shape with sphericity of 0.3~0.5. The sphericity is defined as a ratio of surface area of sphere having the same volume as that of a powder particle to surface area of the powder particle. Here, the surface area of the powder particle is calculated from specific surface area of the powder, and the surface area of sphere having the same volume as that of the powder particle is calculated from diameter per sphere. In the present invention, the sphericity is measured by uniforming size, number, and gravity of the particles by classification of the composite pigment to the particle diameter of 37 μm or less with Mesh No. 400. Namely, BET method is applied to measuring of the specific surface area of the powder and the sphericity can be calculated only therefrom. The composite pigment of the present invention has 0.75~1.8 $m^2/g$ of BET surface area and 0.3~0.5 of sphericity.

The present invention will be described in more detail by way of the following steps.

(1) Step of Reacting Sodium Silicate Solution with Aqueous Sulfuric Solution to Form Silica Gel Slurry:

Sodium silicate solution is introduced into a four-neck reactor and thereto is aqueous sulfuric solution added under stirring at a room temperature until pH of the mixture is 7.0~8.0. After the reaction terminates, the mixture is stood sufficiently, and then is washed and filtered to give silica gel slurry.

(2) Step of Crushing said Silica Gel Slurry to Form the Coarse Silica:

The silica gel slurry obtained in step (1) may be subjected to drying and then crushing, or may be subjected to atomization into water tank through nozzle with diameter of 2.0 mm under pressure of about 4.0 kg/cm$^2$, and then filtration and drying. The former method produces granular particles, while the latter produces bead particles. The obtained coarse silica is classified to groups of 500~600 μm, 600~700 μm, 700~850 μm and 850~1,000 μm with Mesh No. 18, 20, 25, 30 and 35 regulated in ASTM E 11:61. The average particle diameter is ranged from 500 to 1,000 μm.

(3) Step of Grinding said Coarse to Form Flaky Silica:

The grinding step is composed of two process: 1st fine grinding with impact mill and 2nd fine grinding with air current-impact system of air jet mill. The obtained flaky silica has average particle diameter of 5.0~10.0 μm.

(4) Step of Coating said Flaky Silica with Ultrafine Titanium Dioxide to Form Composite Particles:

The flaky silica obtained in step (3) is introduced into distilled water in a reactor, and thereto are added 0.2~0.3 mol/l of urea, 0.3~0.4 mol/l of sulfuric acid and 0.007~0.015 mol/l of titanyl sulfate under stirring. The mixture is heated to a temperature of 60~120° C. to precipitate ultrafine titanium hydroxide on flaky silica, to give composite particles. Then, after washing and drying, the composite particles are baked at a temperature of 700~750° C. to crystallize the titanium hydroxide into rutile type of titanium dioxide. Here, baking may be performed by using rotary kiln. By the above coating method, the obtained composite particles are composed of flaky silica and ultrafine titanium dioxide with average particle diameter of 0.1~0.3 μm coated thereon to a thickness of 0.1~0.5 μm.

In the reaction of the step (4), urea is used for controlling growth rate of particles. That is to say, without urea added, titanium hydroxide is formed only by thermo-hydrolysis of titanium sulfate and at this time, growth rate of titanium hydroxide is so fast that the particles tend to be large or uneven by homogeneous growth and aggregation. In addition to the heterogeneous growth related to the coating, homogeneous nucleation forms single particles of titanium hydroxide. While, with urea added, titanium hydroxide is formed by reaction of titanium sulfate and ammonia formed from urea. At this time, homogeneous nucleation may be suppressed so that titanium hydroxide can be coated compactly on the surface of silica. But, if it is added excessively, formation of titanium hydroxide may be inhibited. Therefore, it is preferable to add urea in an amount of 0.2~0.3 mol/l.

Further, sulfuric acid is used for enhancing dissolution of titanium sulfate. But, if it is added excessively, growth rate of titanium hydroxide may be reduced. Therefore, it is preferable to add sulfuric acid in an amount of 0.3~0.4 mol/l.

Also, for the purpose of obtaining appropriate transmittance to the light with wavelength of 500~780 nm, which is central wavelength region for the skin color, it is preferable to coat titanium dioxide to a thickness of 0.1~0.5 μm. The obtained composite particles have lower reflectance to long wavelength region than to short wavelength region, so as to show color tone close to the skin. In addition, the composite particles can provide screening effect and skin-protecting effect by scattering ultraviolet.

(5) Step of Coating said Composite Particles with Silicon Polymer to give Composite Pigments:

Silicon polymer is used for suppressing photocatalytic activity due to titanium dioxide. Firstly, polydimethylsiloxane is emulsified and then adsorbed onto surface of composite particles, followed by dehydration and drying, and then heating to be fixed. Also, the composite pigment modified by silicon polymer has improved water resistance.

The composite pigments prepared by the method according to the present invention have improved skin-adhesion and spreadability by coating flaky silica with ultrafine titanium dioxide, and appropriate transmittance to central wavelength region for the skin color by coating ultrafine titanium dioxide to a thickness of 0.1~0.5 μm. Further, the composite pigments according to the present invention show light feeling onto the skin and good water resistance.

Further, the present invention provides a make-up cosmetic composition containing the composite pigment produced by the above-described method, in an amount of 0.1~50% by weight, which can be chosen depending on the formulations or the final purposes of the composition. Further, the composition may be formulated, but not limited thereto, emulsified makeup foundation, makeup base, twincakes, compact or skin cover. Also, the compositions may further comprise other components, which have been conventionally used and can be chosen depending on the formulation.

PREFERRED EMBODIMENTS OF THE INVENTION

The present invention will be described in more detail by way of the following examples. However, these examples are provided for only illustration and should not be construed as limiting the scope of the invention, which is properly delineated in the accompanying claims.

EXAMPLE 1

1) Into a four-neck reactor, was introduced 10 l of sodium silicate solution(mole ration of $SiO_2/Na_2O$:3.23, technical grade) containing 10% by weight of silica and thereto was 8% of aqueous sulfuric solution added at a rate of 100 ml/min under stirring at a room temperature, to obtain the solution with pH7.3. After the reaction terminated, the mixture was stood sufficiently and then filtered.

2) The filtrate was washed with 2 4, of distilled water and then filtered to give product of slurry form.

3) The product of the above 2) was poured in plate-form container and dried at a temperature of 100° C. for about 8 hours, to give product of slice form.

4) The product of the above 3) was crushed with a mortar to a particle diameter of 0.5~4 mm and then classified with a sieve to a main particle diameter of 850~1,000 μm.

5) The product of the above 4) was grinded with an impact mill to an average particle diameter of about 100 μm and then with an air current-impact system of air jet mill under a pneumatics of about 6 kg/cm$^2$ to give final flaky silica with average particle diameter of about 10.0 μm.

6) Into another four-neck flask, was distilled water introduced and thereto was the fine silica of the above 5) added to an amount of 20% by weight and then suspended.

7) To the suspension of the above 6), were 0.3 mol/l of urea, 0.35 mol/l of sulfuric acid and 0.008 mol/l of titanium sulfate added under stirring and then heated to a temperature of about 80° C.

8) After the reaction terminated, the mixture was stood overnight, and then washed with distilled water and dried.

Next, the product was baked at a temperature of 700~750° C. to give composite particles of silica and titanium dioxide coated thereon.

At this time, the coated titanium dioxide has the average particle diameter of about 0.1 μm and the coated thickness is about 0.1 μm.

9) 200 g of the composite particles of the above 8) was dispersed in 1 l of distilled water, and then, thereto was 6~10 g of polydimethylsiloxane added at a temperature of 80° C. After the adsorption terminated, the product was anhydrated and dried at a temperature of 150~200° C. to give the surface-modified composite pigments.

The obtained composite pigment has the flaky particles with BET surface area of 1.15 m$^2$/g and sphericity of 0.33, to show good spreadability.

EXAMPLE 2

The same procedure as described in Example 1 was followed by using 0.2 mol/l of urea, 0.35 mol/l of sulfuric acid and 0.011 mol/l of titanium sulfate in the step 7), to give composite pigment of flaky particles with BET surface area of 0.95 m$^2$/g and sphericity of 0.4. The obtained composite pigment showed good spreadability.

EXAMPLE 3

1) Into a four-neck reactor, was introduced 10 l of sodium silicate solution(mole ratio of SiO$_2$/Na$_2$O:3.23, technical grade) containing 10% by weight of silica and thereto was 8% of aqueous sulfuric solution added at a rate of 100 ml/min under stirring at a room temperature to obtain the solution with pH7.5. After the reaction terminated, the mixture was stood sufficiently and then filtered.

2) The filtrate was washed with 2 l of distilled water and then filtered to give product of slurry form.

3) The product of the above 2) was atomized into water tank through nozzle with diameter of 2.0 mm under pressure of about 4.0 kg/cm$^2$ at a temperature of about 40° C., and then filtered and washed with 4 l of distilled water.

4) The product of the above 3) was filtered and dried at a temperature of 100° C. for about 8 hours, to give product of bead form. Then, the bead product was classified with a sieve to a main particle diameter of 600~700 μm.

5) The product of the above 4) was grinded with an impact mill to an average particle diameter of about 50 μm and then with an air current-impact system of air jet mill under a pneumatics of about 7 kg/cm$^2$ to give final flaky silica with average particle diameter of about 5.0 μm.

6) Into another four-neck flask, was distilled water introduced and thereto was the fine silica of the above 5) added to an amount of 20% by weight and then suspended.

7) To the suspension of the above 6), were 0.2 mol/l of urea, 0.35 mol/l of sulfuric acid and 0.014 mol/l of titanium sulfate added under stirring and then heated to a temperature of about 80° C.

8) After the reaction terminated, the mixture was stood overnight, and then washed with distilled water and dried. Next, the product was baked at a temperature of 700~750° C. to give composite particles of silica and titanium dioxide coated thereon. At this time, the coated titanium dioxide has the average particle diameter of about 0.3 μm and the coated thickness is about 0.3 μm.

9) 200 g of the composite particles of the above 8) was dispersed in 1 l of distilled water, and then, thereto was 6~10 g of polydimethylsiloxane added at a temperature of 80° C. After the adsorption terminated, the product was anhydrated and dried at a temperature of 150~200° C. to give the surface-modified composite pigments.

The obtained composite pigment has the flaky particles with BET surface area of 1.5 m$^2$/g and sphericity of 0.5, to show good spreadability.

The whiteness and the optical property of the composite pigments prepared in the above Examples 1 to 3 were evaluated. The results are shown in Experimental Examples 1 and 2.

Experimental Example 1 Whiteness of the Pigments

In order to evaluate evenness of film of the composite pigments on the skin, 0.02 g of the composite pigments was applied on the skin having 30 cm$^2$ of area from the center to the outer drawing concentric circles. The whiteness was measured at a distance of 0 cm, 0.5 cm, 1.0 cm, 1.5 cm, 2.0 cm from the center to the right and to the left, respectively with SpectroGuard ∥ Color System(Pacific Scientific, USA). The results are shown in FIG. 1 and the whiteness of the naked skin is about 65.

In FIG. 1, "●" indicates the whiteness of each location to be applied; "▲" indicates the whiteness of each location applied with the composite pigments of Example 1; "♦" indicates the whiteness of each location applied with the composite pigments of Example 2; and "■" indicates the whiteness of each location applied with the composite pigments of complete spherical silica and titanium dioxide coated thereon(TCRAYCERAM S-IT, Japan Toray Industries, Inc.).

As apparent from FIG. 1, it was observed that the whiteness indicated by "■" becomes higher to the outer from the center. From this result, it may be understood that the film of the composite pigments was maldistributed to the outer along the direction of force to be applied, and this maldistritution is caused by excessive fluidity of the spherical particles. While, it was observed that the composite pigments with sphericity of 0.33("▲") and with sphericity of 0.4("♦") was applied evenly and the whiteness of the film thereof is similar to that of the naked skin. From this result, it may be understood that the flaky composite pigments is applied glidingly onto the skin, to enable fluidity and skin-adhesion force controlled.

Experimental Example 2 Optical Property of the Pigments

In order to evaluate optical property of the composite pigments, dispersions to be applied were prepared. As film forming-agent, 1:10 admixture of polyvinylpyrrolidone and isopropyl alcohol was used. The dispersions were prepared by dispersing the flaky silica prepared in the step 5) of Example 1, and composite pigments of Examples 1, 2, and 3, respectively in the above admixture. The dispersions were pasted on black plate at a thickness of 100 μm with a film applicator. At this time, the light transmitting the pasted film is absorbed by the black plate so that only the amount of the light not to be transmitted can be measured. Reflectance was measured in wavelength region for visible light with spectrophotometer Cary5E(Varian). The results are shown in FIG. 2.

Figure 2:
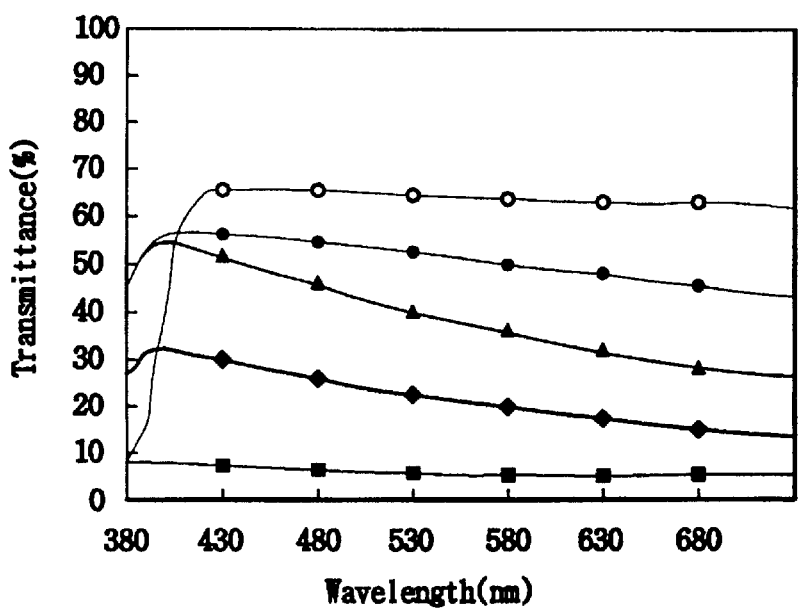
FIG. 2 is a graph showing percent transmittance at various wavelengths for different composite pigments.

In FIG. 2, "■" indicates the reflectance of the film formed by the flaky silica prepared in the step 5) of Example 1; "♦" indicates the reflectance of the film formed by the composite pigments of Example 1; "▲" indicates the reflectance of the film formed by the composite pigments of Example 2; "●" indicates the reflectance of the film formed by the composite pigments of Example 3; and "○" indicates the reflectance of the film formed by the composite pigments of complete spherical silica and titanium dioxide coated thereon (TORAYCERAM S-IT, Japan Toray Industries, Inc.).

As apparent from FIG. 2, it was observed that the composite pigments having spherical particles("○") has excessive masking effect to cause albinism, and the single powder of flaky silica("■") has weak masking effect to be ineffective in masking the defect such as freckle. While, it was observed that the flaky composite pigments of the present invention("♦", "▲" and "●") have appropriate transmittance to the light of 500~780 nm, which is central wavelength region for the skin color, and so is expected to increase chroma of the skin color to express light and healthy skin-color tune. In addition, it may be understood that, compared with the reflectance to the wavelength region of 400 nm or lower, the flaky composite pigments have more excellent UV-shielding effect than that of the spherical composite pigments. The reason may be guessed that the flaky composite particles form compacter film and area occupied by titanium dioxide of the flaky particles is larger.

The make-up cosmetic composition containing the composite pigments of the present invention will be described in more detail by way of the following formulations 1~3. However, these formulations are provided only for illustration purpose and should not be construed as limiting the scope of the invention, which is properly delineated in the accompanying claims.

<Formulations 1~3 and Comparative Formulation> Twincakes

| Materials | Formulation 1 | Formulation 2 | Formulation 3 | Comparative Formulation |
|---|---|---|---|---|
| 1. Talc | to 100 | to 100 | to 100 | to 100 |
| 2. Sericite | 15 | 15 | 15 | 15 |
| 3. Mica | 10 | 10 | 10 | 10 |
| 4. Kaolin | 4 | 4 | 4 | 4 |
| 5. Calcium carbonate | 2 | 2 | 2 | 2 |
| 6. Composite pigment of Ex. 1 | 15 | — | — | — |
| 7. Composite pigment of Ex. 2 | — | 15 | — | — |
| 8. Composite pigment of Ex. 3 | — | — | 15 | — |
| 9. Titanium dioxide | — | — | — | 15 |
| 10. Ferric oxide | 8 | 8 | 8 | 8 |
| 11. Liquid paraffin | 5 | 5 | 5 | 5 |
| 12. Preservative | 0.15 | 0.15 | 0.15 | 0.15 |
| 13. Perfume | 0.3 | 0.3 | 0.3 | 0.3 |

Preparation (1) The materials #1 to 10 were mixed.

(2) The materials #11 to 13 were dissolved at a temperature of 80° C.

(3) The above (2) was sprayed to the above (1), and then mixed and pulverized and crushed, and molded to give a twincake.

Experimental Example 3

In order to evaluate spreadability, skin-adhesion, masking effect, skin-color tune expression and water resistance, 50 females aging 25~35 years used the twincakes of Formulations 1~3 and Comp. Formulation, respectively, to give scores. Evaluation scores are as follows:

5: Excellent 4: Good 3: Average 2: Poor 1: Very poor
The results are shown in Table 1.

TABLE 1

| | Spreadability | Skin-adhesion | Masking effect | Skin-color tune expression | Water resistance |
|---|---|---|---|---|---|
| Formulation 1 | 5 | 4 | 2 | 3 | 5 |
| Formulation 2 | 5 | 5 | 3 | 5 | 5 |
| Formulation 3 | 4 | 5 | 4 | 3 | 5 |
| Comp. Formulation | 2 | 4 | 5 | 2 | 3 |

As shown in Table 1, the twincakes containing the composite pigments of the present invention have improved spreadability and skin-adhesion, and good skin-color tune expression. In addition, the twincakes of the present invention have excellent water resistance. And, the user said that the twincakes of Formulations 1~3 are light in feel.

What is claimed is:

1. A method of preparing composite pigments for make-up cosmetics, comprising the steps of:
   (1) reacting a sodium silicate solution with an aqueous sulfuric acid solution to form a silica gel slurry;
   (2) crushing said silica gel slurry to form coarse silica;
   (3) grinding said coarse silica by means of an impact mill followed by fine grinding with an air current impact system of an air jet mill to form flaky silica;
   (4) coating said flaky silica with ultrafine titanium dioxide to form composite particles by admixing said flaky silica (3) with 0.2~0.3 mol/l of urea, 0.3~0.4 mol/l of sulfuric acid and 0.007~0.015 mol/l of titanyl sulphate in distilled water, then heating, washing and drying, and then baking; and
   (5) coating the resultant baked composite particles with silicon polymer to give said composite pigments.

2. The method according to claim 1, wherein said coarse silica of said step (2) has granular particles.

3. The method according to claim 2, wherein said granular particles are prepared by drying said silica gel slurry and then crushing.

4. The method according to claim 1, wherein said coarse silica of said step (2) has bead particles.

5. The method according to claim 4, wherein said bead particles are prepared by atomizing said silica gel slurry into water tank, and then filtering and drying.

6. The method according to claim 1, wherein said flaky silica of said step (3) has average particle diameter of 5.0~10 $\mu$m.

7. The method to claim 1, wherein said titanium dioxide is coated to a thickness of 0.1~0.5 $\mu$m.

8. The method according to claim 1, wherein said titanium dioxide has average particle diameter of 0.1~0.3 $\mu$m.

9. The method according to claim 7, wherein said titanium dioxide has average particle diameter of 0.1~0.3 $\mu$m.

10. A composite pigment prepared by the method according to claim 1.

11. A make-up cosmetic composition comprising said composite pigments claimed in claim 10 in an amount of 0.1~50% by weight.

12. The make-up cosmetic composition according to claim 11, wherein said composition is formulated as an emulsified makeup foundation, makeup base, twincakes, compact or skin cover.

* * * * *